US010856809B2

(12) United States Patent
Boesen

(10) Patent No.: US 10,856,809 B2
(45) Date of Patent: Dec. 8, 2020

(54) EARPIECE WITH GLUCOSE SENSOR AND SYSTEM

(71) Applicant: BRAGI GmbH, Munich (DE)

(72) Inventor: Peter Vincent Boesen, Munich (DE)

(73) Assignee: BRAGI GmbH, Munich (DE)

( * ) Notice: Subject to any disclaimer, the term of this patent is extended or adjusted under 35 U.S.C. 154(b) by 187 days.

(21) Appl. No.: 15/464,810

(22) Filed: Mar. 21, 2017

(65) Prior Publication Data

US 2017/0273625 A1    Sep. 28, 2017

Related U.S. Application Data

(60) Provisional application No. 62/312,593, filed on Mar. 24, 2016.

(51) Int. Cl.
*A61B 5/00* (2006.01)
*H04R 1/10* (2006.01)
(Continued)

(52) U.S. Cl.
CPC .......... *A61B 5/6817* (2013.01); *A61B 5/1455* (2013.01); *A61B 5/14532* (2013.01);
(Continued)

(58) Field of Classification Search
CPC . A61B 5/6817; A61B 5/6815; A61B 5/14532; A61B 5/1455; H04R 1/028; H04R 1/1016; H04R 1/1041; H04R 2402/07
See application file for complete search history.

(56) References Cited

U.S. PATENT DOCUMENTS 3,934,100 A    1/1976   Harada
4,150,262 A    4/1979   Ono
(Continued)

FOREIGN PATENT DOCUMENTS

CN    204244472 U    4/2015
CN    104683519 A    6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — Matthew Kremer
*Assistant Examiner* — Avery M Foley
(74) *Attorney, Agent, or Firm* — Goodhue, Coleman & Owens, P.C.

(57) ABSTRACT

An earpiece may include an earpiece housing, an intelligent control disposed within the earpiece housing, and a glucose sensor operatively connected to the intelligent control. The intelligent control may be configured to determine glucose levels associated with a user of the earpiece using the glucose sensor. The earpiece may further include a wireless transceiver disposed within the earpiece housing, the wireless transceiver operatively connected to the intelligent control. The glucose sensor may be a non-invasive glucose sensor such as a near infrared glucose sensor. The earpiece housing may be configured to position the glucose sensor against a wall of the external auditory canal.

10 Claims, 6 Drawing Sheets

(51) Int. Cl.
*A61B 5/145* (2006.01)
*A61B 5/1455* (2006.01)
*H04R 1/02* (2006.01)

(52) U.S. Cl.
CPC ............ *H04R 1/028* (2013.01); *H04R 1/1016* (2013.01); *H04R 1/1041* (2013.01); *H04R 2420/07* (2013.01)

(56) References Cited

U.S. PATENT DOCUMENTS

| | | |
|---|---|---|
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B1 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,825,626 B2 | 11/2010 | Kozisek |
| 7,979,035 B2 | 7/2011 | Griffin et al. |
| 7,983,628 B2 | 7/2011 | Boesen |
| 8,095,188 B2 | 1/2012 | Shi |
| 8,140,357 B1 | 3/2012 | Boesen |
| 8,300,864 B2 | 10/2012 | Müllenborn et al. |
| 8,436,780 B2 | 5/2013 | Schantz et al. |
| 8,719,877 B2 | 5/2014 | VonDoenhoff et al. |
| 8,891,800 B1 | 11/2014 | Shaffer |
| 8,994,498 B2 | 3/2015 | Agrafioti et al. |
| 9,013,145 B2 | 4/2015 | Castillo et al. |
| 9,037,125 B1 | 5/2015 | Kadous |
| 9,081,944 B2 | 7/2015 | Camacho et al. |
| 9,510,159 B1 | 11/2016 | Cuddihy et al. |
| 9,579,060 B1* | 2/2017 | Lisy ............... A61B 5/6803 |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0258412 A1 | 11/2006 | Liu |
| 2008/0090622 A1 | 4/2008 | Kim et al. |
| 2008/0146890 A1 | 6/2008 | LeBoeuf et al. |
| 2008/0254780 A1 | 10/2008 | Kuhl et al. |
| 2009/0017881 A1 | 1/2009 | Madrigal |
| 2009/0073070 A1 | 3/2009 | Rofougaran |
| 2009/0296968 A1 | 12/2009 | Wu et al. |
| 2010/0033313 A1 | 2/2010 | Keady et al. |
| 2010/0203831 A1 | 8/2010 | Muth |
| 2010/0320961 A1 | 12/2010 | Castillo et al. |
| 2011/0218489 A1* | 9/2011 | Mastrototaro ..... A61B 5/14532 604/66 |
| 2011/0286615 A1 | 11/2011 | Olodort et al. |
| 2014/0122116 A1 | 5/2014 | Smythe |
| 2014/0163771 A1 | 6/2014 | Demeniuk |
| 2014/0185828 A1 | 7/2014 | Helbling |
| 2014/0222462 A1 | 8/2014 | Shakil et al. |
| 2014/0270227 A1 | 9/2014 | Swanson |
| 2014/0270271 A1 | 9/2014 | Dehe et al. |
| 2015/0028996 A1 | 1/2015 | Agrafioti et al. |
| 2015/0148989 A1 | 5/2015 | Cooper et al. |
| 2015/0245127 A1 | 8/2015 | Shaffer |
| 2016/0033280 A1 | 2/2016 | Moore et al. |
| 2016/0073189 A1 | 3/2016 | Lindén et al. |
| 2016/0206232 A1* | 7/2016 | Bordelon ............ A61B 5/1455 |
| 2016/0287087 A1* | 10/2016 | Abreu ................... A61B 5/01 |

(56) References Cited

U.S. PATENT DOCUMENTS

| | | | |
|---|---|---|---|
| 2017/0000359 A1* | 1/2017 | Kohli | A61B 5/02055 |
| 2017/0014056 A1* | 1/2017 | Newberry | A61B 5/14532 |
| 2017/0164878 A1* | 6/2017 | Connor | G09B 23/28 |

FOREIGN PATENT DOCUMENTS

| | | |
|---|---|---|
| CN | 104837094 A | 8/2015 |
| EP | 1017252 A2 | 7/2000 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected-The personalized digital assistant", "http://bmwblog.com/2016/01/05/bmw-introduces-bmw-connected-the-personalized-digital-assistant", (Jan. 5, 2016).
BRAGI Is on Facebook (2014).
BRAGI Update—Arrival of Prototype Chassis Parts—More People—Awesomeness (May 31, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16,2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Califorma (2017).
Last Push Before The Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & the BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).

* cited by examiner

EARPIECE WITH GLUCOSE SENSOR AND SYSTEM

PRIORITY STATEMENT

This application claims priority to U.S. Provisional Patent Application 62/312,593, filed on Mar. 24, 2016, and Earpiece with glucose sensor and system, hereby incorporated by reference in its entirety.

BACKGROUND

I. Field of the Disclosure

The illustrative embodiments relate to wearable devices. More particularly, but not exclusively, the illustrative embodiments relate to earpieces.

II. Description of the Art

The growth of wearable devices is increasing exponentially. This growth, is fostered by the decreasing size of microprocessors, circuity boards, chips, and other components. The ear and ear canal provide a potentially rich environment for the collection of biometric data through the use of wearable devices and, particularly, earpieces. One reason that the ear is a rich environment for the collection of biometric data is that the ear and ear canal have a rich blood supply at or near the surface of the skin. The blood supply is rich with a variety of biological compounds, including glucose. The detection and measurement of glucose is important in many users, but especially those users and patients who are susceptible to or are diagnosed with diabetes. Historically, glucose detection has required invasive technologies to assist the user in obtaining an accurate measurement of blood glucose levels. More recently, however, technology and sensors are being developed which allow for non-invasive approaches to blood glucose monitoring. What is needed is an approach to utilize an earpiece sensor and system for the detection of glucose levels of the user.

SUMMARY OF THE DISCLOSURE

Therefore, it is a primary object, feature, or advantage to improve over the state of the art.

It is a further object, feature, or advantage to provide an earpiece sensor and system for the detection of glucose in the user.

It is a still further object, feature, or advantage is to report the glucose level to the user.

One or more of these and/or other objects, features, or advantages will become apparent from the specification and claims that follow. No single embodiment need provide each or every one of these objects, features, or advantages. Instead, different embodiments may have different objects, features, or advantages. The present invention is not to be limited by or to these objects, features, and advantages.

According to one aspect a wearable device includes a wearable device housing, an electronics package associated with the wearable device housing, and a glucose sensor associated with the earpiece housing. The glucose sensor may be a part of the electronics package. The glucose sensor may be distal to the electronics package and proximate to the opening in the earpiece. The glucose sensor may be non-invasive and may provide continuous monitoring of glucose levels. The glucose sensor may use near infrared sensors.

According to another aspect, an earpiece may include an earpiece housing, an electronics package associated with the earpiece housing, and a glucose sensor associated with the earpiece housing. The glucose sensor may be a part of the electronics package. The glucose sensor may be distal to the electronics package and proximate to the opening in the earpiece. The glucose sensor may be non-invasive and may provide continuous monitoring of glucose levels. The glucose sensor may use near infrared sensors.

According to another aspect, an earpiece includes an earpiece housing, an intelligent control disposed within the earpiece housing, and a glucose sensor operatively connected to the intelligent control. The intelligent control may be configured to determine glucose levels associated with a user of the earpiece using the glucose sensor. The earpiece may further include a wireless transceiver disposed within the earpiece housing, the wireless transceiver operatively connected to the intelligent control. The glucose sensor may be a non-invasive glucose sensor such as a near infrared glucose sensor. The earpiece housing may be configured to position the glucose sensor against a wall of the external auditory canal.

According to another aspect, a method of glucose monitoring of an individual using an earpiece includes providing the earpiece, the earpiece comprising an earpiece housing, an intelligent control disposed within the earpiece housing, and a glucose sensor operatively connected to the intelligent control. The method may further include sensing glucose levels of the individual at an ear of the user using the glucose sensor of the ear piece. The method may further include wirelessly communicating a glucose level of the individual from the earpiece to a mobile device using a wireless transceiver disposed within the earpiece housing, the wireless transceiver operatively connected to the intelligent control.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

Figure 1:
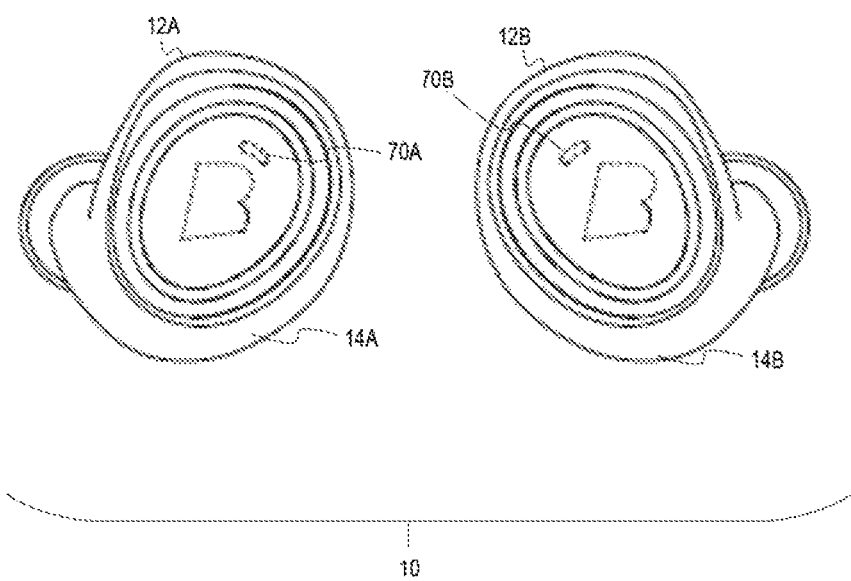
FIG. 1 is a pictorial representation of a communication system in accordance with an illustrative embodiment.

The illustrative embodiments provide a device and system for detecting glucose in a user. The electronics package of wearable devices often contains sensors including temperature sensors, pulse oximeters, accelerometers, gyroscopes, altitude sensors, GPS chips, and so forth. The sensors may be utilized to sense any number of biometric readings or information, such as heart rate, respiratory rate, blood, or skin physiology, or other biometric data.

One location that is used for the collection of biological information is the ear and the auditory canal. The external auditory canal sits in close proximity to the central nervous system and has a rich blood supply. For example, the superficial temporal artery, the deep auricular artery, the stylomastoid artery, and the posterior auricular artery all provide the ear, ear canal, and inner ear with blood. Because the ear has an abundant and rich blood supply, it is a good location for the detection and measurement of biologic compounds related to the blood.

One such compound found in the blood is glucose. Glucose is a product of the breakdown of carbohydrate rich foods and is the main source of energy used by the body. Glucose is regulated throughout the body by the production of insulin at the pancreas. When the amount of blood glucose rises, the pancreas releases insulin to help maintain proper blood glucose levels. The inability to regulate blood glucose levels can result in hypoglycemia (too little blood glucose) or hyperglycemia (too much blood glucose). This can be caused by a variety of factors, but prolonged variances in blood glucose are typically caused by the inadequate production of insulin or the body's cells improperly responding to the presence of insulin. In such cases, the glucose levels of the blood begin to increase, causing any minter of biological and metabolic issues for the patient/user. This group of metabolic disease related to insulin production and blood glucose levels is often referred to as diabetes.

It is, therefore, advantageous to monitor blood glucose levels in all users, especially those diagnosed with, or having a history of, diabetes. Monitoring blood glucose can allow users to anticipate changes in blood glucose which may be indicative of diabetes. Additionally, those users who have been diagnosed with diabetes are required to constantly measure their blood glucose and administer insulin accordingly in an effort to keep blood glucose levels within a healthy range. Historically, glucose monitoring methods have been invasive and delayed. Often the monitoring methods require the user to prick their skin and measure glucose levels through a drop of blood. However, as technology related to blood glucose improves, more non-invasive techniques for the measurement of blood glucose have been developed.

Recently, new technologies have been introduced for the detection of blood glucose levels which do not require direct access to blood. These technologies include near Infra-red (near IR) detection, ultrasound, wave-modulated differential laser photothermal radiometry (WM-DPTR), and dielectric spectroscopy. In addition to being non-invasive, these methods provide a continuous approach to blood glucose monitoring, as compared to the single measurement provided by the more invasive methods. Adapting and employing these techniques and sensors the blood rich environment of the ear and ear canal can provide continuous, non-invasive approach to monitoring blood glucose levels.

In one embodiment, a glucose sensor would be incorporated into the wireless earpieces. The wireless earpieces run include an earpiece housing and a glucose sensor associated with the earpiece housing. The glucose sensor would be positioned advantageously, such that when the user places the wireless earpiece into the ear and ear canal, the glucose sensor is situated in position to best measure the blood glucose levels of the user. The glucose sensor may be placed such that the portion of the sensor which may emit detection signals is positioned closest to the blood supply of the user. The glucose sensor may be positioned as proximate to the opening of the wireless earpieces as possible while allowing for accurate glucose monitoring. In some cases, the glucose sensor may or may not be used in tandem with an included electronics packet. In some cases, the position for the best glucose measurement may require the glucose sensor to be positioned apart from an included electronics packet.

In another embodiment, a glucose sensor would be incorporated into an electronics packet of wireless earpieces. The electronics packet may include additional sensors and electronic equipment. The glucose sensor would be positioned within the electronics packet such that the glucose sensor would be in contact with the outer wall of the wireless earpiece housing and in a manner that allowed the glucose sensor direct access to the user's ear or ear canal. Such position would allow the glucose sensor access to the blood supply of the user and the ability to measure the user's glucose level.

FIG. 1 illustrates a set of earpieces 10 including a left earpiece 12A and a right earpiece 12B. The left earpiece 12A has a housing or casing 14A and the right earpiece 12B has a housing or casing 14B. A microphone 70A is shown on the left earpiece 12A and a microphone 70B is shown on the right earpiece 12B. Not shown in FIG. 1, one or both of the earpieces may include a glucose sensor. Where glucose sensors are present in both earpieces 10, glucose data from the different sensors may be compared to determine differences in sensed glucose data which may potentially be used to increase accuracy, and/or detect error.

Figure 2:
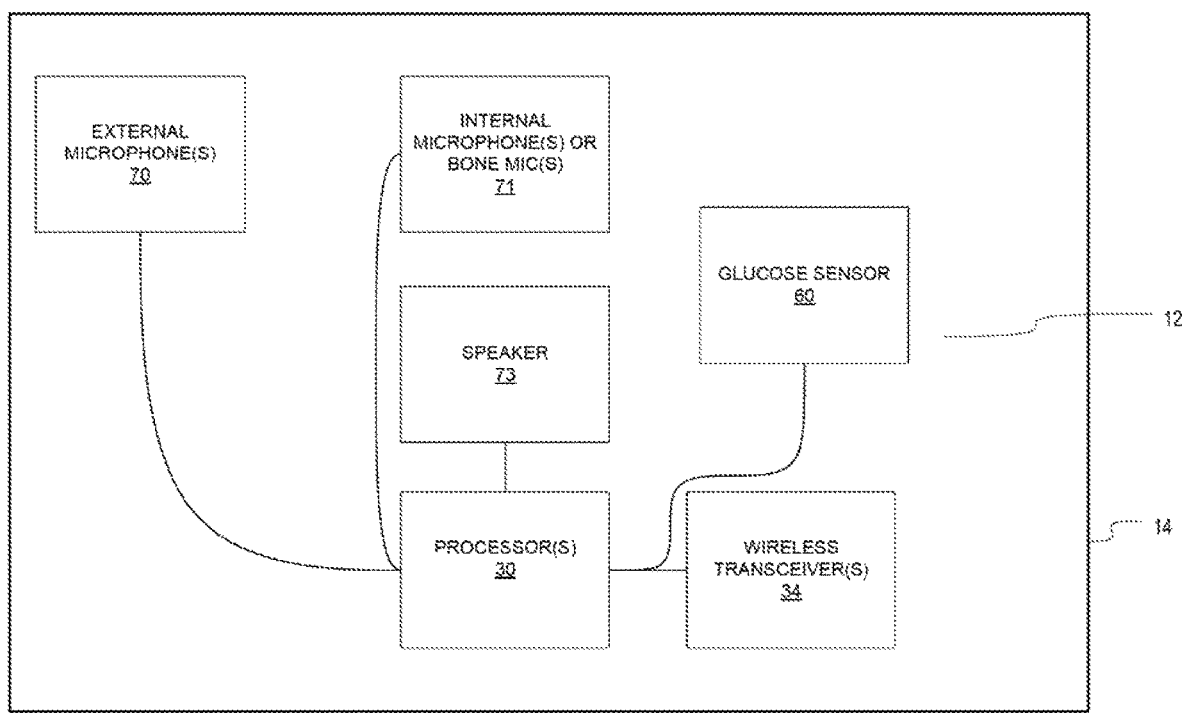
FIG. 2 is a block diagram of wireless earpieces in accordance with an illustrative embodiment.

FIG. 2 illustrates an earpiece 12 which may be a left earpiece or a right earpiece. One or more processors or other intelligent controls 30 are shown disposed within the housing 14 of the earpiece. One or more wireless transceivers 34 are operatively connected to the processors 30. The term "processor" as used herein means a single processor or more than one processor in operative communication. The processor may include a digital signal processor, a microprocessor and/or other types of processors. The term intelligent control is used herein to encompass one or more processors. The wireless transceivers 34 may include a BLUETOOTH transceiver, an ultra-wideband (UWB) transceiver, or type of radio transceiver, a near field magnetic induction (NFMI) transceiver, or other type of transceiver. One or more external microphones 70 is operatively connected to the processors 30 as are one or more internal microphones or bone microphones 71. A glucose sensor 60 is disposed within the housing 14 of the earpiece 12. The glucose sensor 60 is operatively connected to the processor(s) 30 to communicate sensed glucose data sensed at the ear of a user of the earpiece to the processor(s) 30.

Figure 3:
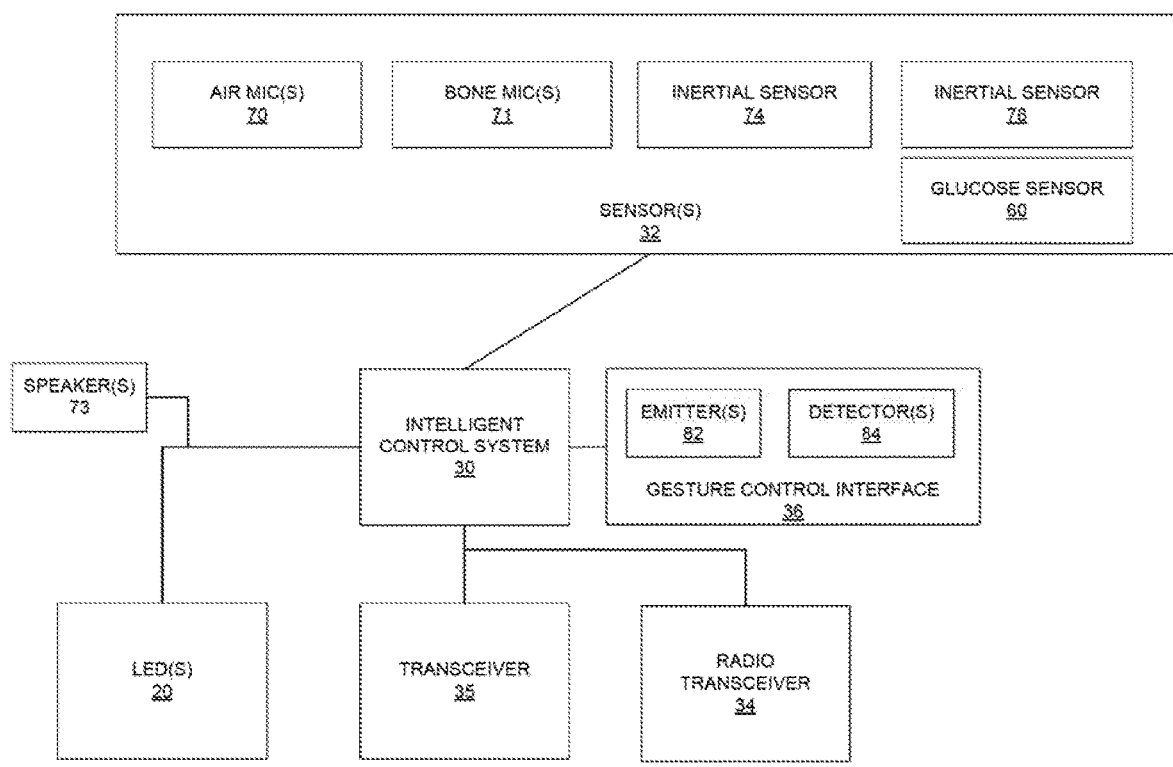
FIG. 3 is a block diagram of wireless earpieces in accordance with an illustrative embodiment.

FIG. 3 is a block diagram illustrating an earpiece. The earpiece may include one or more sensors 32. The sensors may include one or more air microphones 70, one or more bone microphones 71, and one or more inertial sensors 74, 76. Each of the one or more sensors 32 is operatively connected to an intelligent control system 30. The intelligent control system 30 may also be operatively connected to a gesture control interface 36 which may include one or more emitters 82 and one or more detectors 84. The gesture control interface 36 allows a user to interact with the earpiece through gestures or motions which are detected by the gesture control interface and interpreted by the intelligent control system 30. One or more speakers 72 is operatively connected to the intelligent control system 30. One or more light emitting diodes 20 are operatively connected to the intelligent control system 30 that may be used to provide visual feedback indicative of earpiece functionality or status. A radio transceiver 34 is shown as well as a second transceiver 35 which may be an NFMI transceiver or other type of transceiver. A glucose sensor 60 is operatively connected to the intelligent control system 30.

Figure 4:
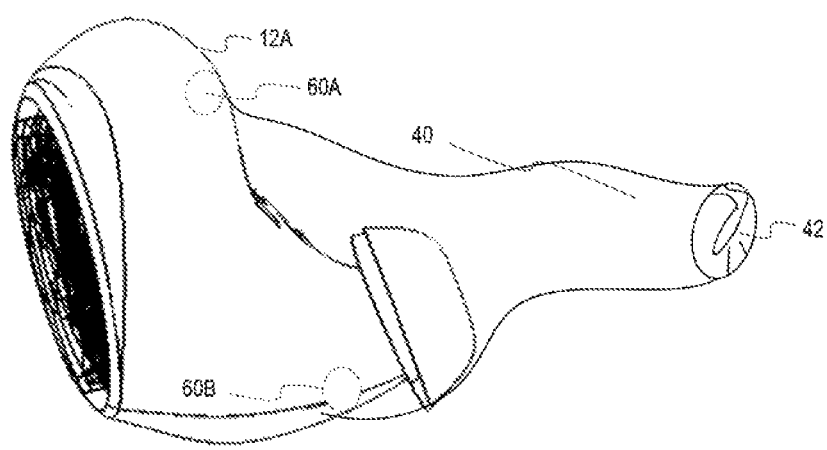
FIG. 4 is a pictorial representation of wireless earpieces in accordance with an illustrative embodiment.

FIG. 4 illustrates one example of an earpiece 12A positioned within the external auditory canal 40 of an individual using the earpiece 12A. The earpiece 12A as shown isolates or serves as a barrier between the ambient environment and the external auditory canal 40. A tympanic membrane 42 is shown positioned at the end of the external auditory canal 40. One or more glucose sensors 60A, 60B are present. The glucose sensor is placed in a position which provides access to a blood supply suitable for using to determine glucose levels in the blood. For example, the glucose sensor 60A may be positioned proximate the superficial temporal artery near the superior wall of the external auditory canal. The glucose 60B may be positioned proximate the superficial temporary artery and the stylomastoid artery near the inferior wall of the external auditory canal. It is contemplated that the glucose sensor may be positioned in other locations at or near the ear as may be appropriate based on the configuration of the earpiece relative to the arteries associated with the ear and/or nearby regions.

Figure 5:
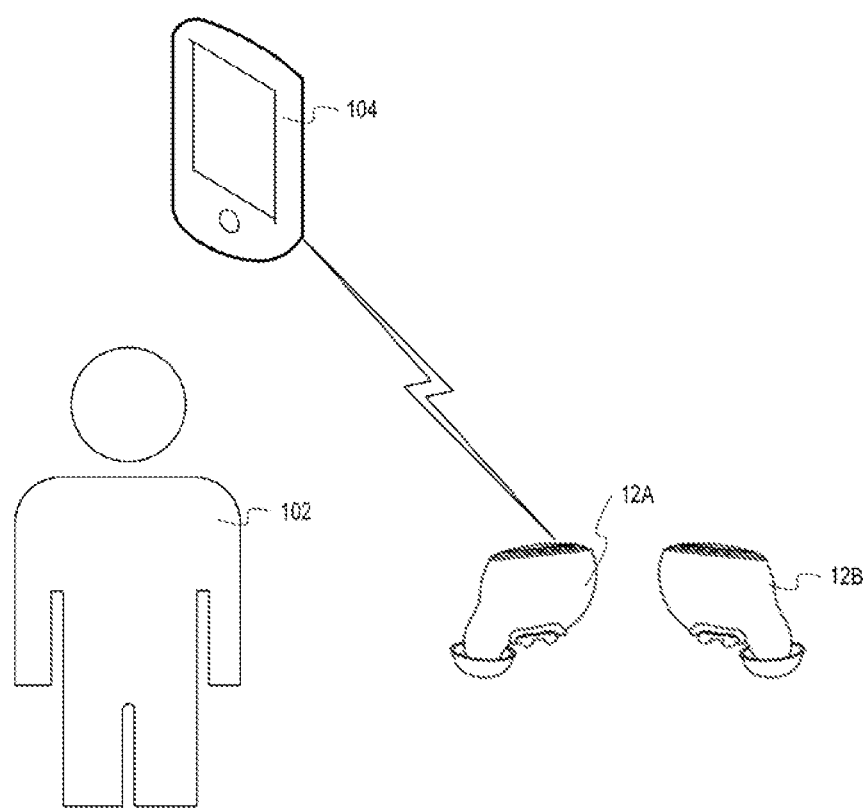
FIG. 5 is a pictorial representation of a communication system in accordance with an illustrative embodiment.

FIG. 5 is a pictorial representation of a system in accordance with an illustrative embodiment. In one embodiment, the communication system may include one or more wireless earpieces 12A, 12B which may be worn by a user 102 and wireless device 104. The wireless earpieces 12A, 12B may be referred to as a pair or set or singularly (wireless earpiece). In one embodiment, the wireless earpieces 12A, 12B include a left earpiece and a right earpiece configured to fit into a user's 102 ears. The wireless earpieces 12A, 12B are shown separately from their positioning within the ears of the user 102 for purposes of simplicity. The wireless earpieces 12A, 12B may be configured to play music or audio, receive and make phone calls or other communications, determine ambient environmental readings (e.g., temperature, altitude, location, speed, heading, etc.), read user biometrics and actions (e.g., heart rate, motion, sleep, blood oxygenation, calories burned, etc.). The wireless earpieces 12A, 12B may also be fitted with a glucose sensor for detecting blood glucose levels of the user 102. The wireless earpieces 12A, 12B may having a housing sized and shaped to lit a portion of the earpiece housing into the external auditory canal. The earpiece housing may be an ear bud type or style of housing The wireless earpieces 12A, 12B may include interchangeable parts that may be adapted to lit the needs of the user 102. For example, sleeves that fit into die ear of the user 102 may be interchangeable to find a suitable shape and configuration. The wireless earpieces 12A, 12B may include a number of sensors and input devices including, but not limited to, pulse oximeters, microphones, pulse rate monitors, accelerometers, gyroscopes, light sensors, global positioning sensors, glucose sensors, and so forth. Sensors of the wireless device 104 may also be configured to wirelessly communicate with the wireless earpieces 12A, 12B.

The wireless device 104 may represent any number of wireless electronic devices, such as smart phones, laptops, gaming devices, music players, personal digital assistants, vehicle systems, or so forth. The wireless device 104 may communicate utilizing any number of wireless connections, standards, or protocols near field communications, Bluetooth, Wi-Fi, ANT+, etc.). For example, the wireless device 104 may be a touch screen cellular phone that communicates with the wireless earpieces 12A, 12B utilizing Bluetooth communications. The wireless device 104 may implement and utilize any number of operating systems, kernels, instructions, or applications that may make use of the sensor data measured by the wireless earpieces 12A, 12B. For example, the wireless device 104 may represent any number of android, iOS, Windows, open platform, or other systems. Similarly, the wireless device 104 may include a number of applications that utilize the biometric data from the wireless earpieces 12A, 12B to display applicable information and data. For example, the information (including, high, low, average, or other values) may be processed by the wireless earpieces 12A, 12B or the wireless device 104 to display heart rate, blood oxygenation, altitude, speed, distance traveled, calories burned, or other applicable information.

Sensor measurements made by either the 12A, 12B, wireless device 104, or sensor devices of the user 102 may be communicated with one another. The wireless device 104 is representative of any number of personal computing, communications, exercise, medical, or entertainment devices that may communicate with the wireless earpieces 12A, 12B.

The user 102 may also be wearing or carrying any number of sensor-enable devices, such as heart rate monitors, pacemakers, smart glasses, smart watches, bracelets (e.g., Apple watch, Fitbit, etc.), or other sensory devices that may be worn, attached to, or integrated with the user 102. The data and information from the external sensor devices may be communicated to the wireless earpieces 12A, 12B.

The sensors of the wireless earpieces 12A, 12B may also be positioned at enantiomeric locations. For example, a number of colored light emitting diodes may be positioned to provide variable data and information, such as heart rate, respiratory rate, glucose levels, and so forth. The data gathered by the LED arrays may be sampled and used alone or in aggregate with other sensors. As a result, sensor readings may be enhanced and strengthened with additional data.

Figure 6:
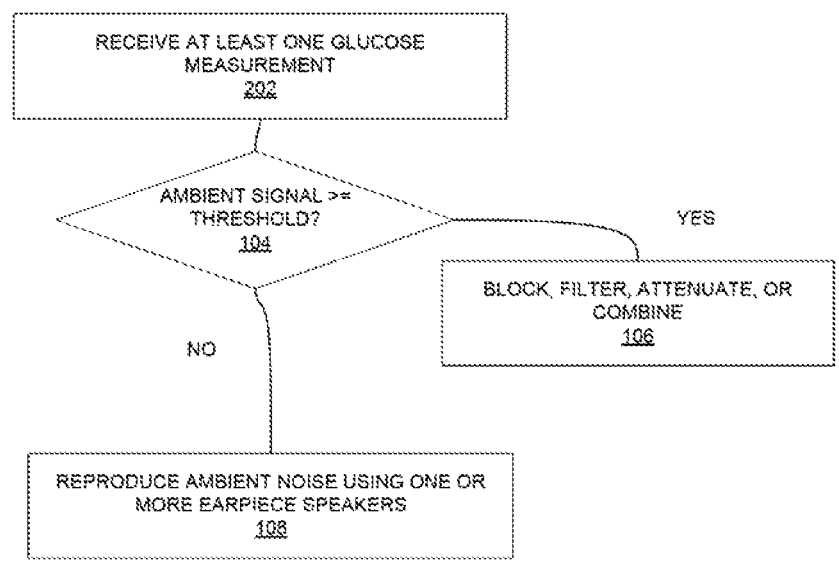
FIG. 6 is a block diagram of a communication system in accordance with an illustrative embodiment.

FIG. 6 is a block diagram illustrating a communication system. The communication system may receive at least glucose measurement 202 from the communication system. After receiving the glucose measurement 202, the communication system may compare the glucose measurement to a threshold biological glucose level 104. For example, the glucose measurement 202, may be compared to a threshold level for a user to determine whether the glucose measurement exceeds the normal range for that user 204. If the glucose measurement 202 is greater than or equal to the normal biological threshold for the user 204, the communication system may be configured to provide the user with a warning, signal, or other indication that the glucose measurement is at or above the biological threshold 206. If the glucose measurement is less than the biological threshold, the communication system may be configured to record the glucose measurement for the user 208. The glucose measurement is also recorded in the event the user is provided with a warning, signal or other indication 206, 208. The communication system may then receive another glucose measurement 202 to provide continuous feedback to a user.

The illustrative embodiments are not to be limited to the particular embodiments described herein. In particular, the illustrative embodiments contemplate numerous variations in the type of ways in which embodiments may be applied. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A set of wireless earpieces having a first earpiece and a second earpiece, each of the first earpiece and the second earpiece comprising:
   an earpiece housing, the earpiece housing configured as an ear bud and sized and shaped to fit a portion of the earpiece housing into an external auditory canal;
   an intelligent control disposed within the earpiece housing;
   a glucose sensor operatively connected to the intelligent control and positioned to fit against a wall of the external auditory canal;
   wherein the intelligent control of the first earpiece is configured to determine a first glucose level associated with a user of the set of earpieces using the glucose sensor of the first earpiece;
   wherein the intelligent control of the second earpiece is configured to determine a second glucose level associated with the user of the set of earpieces using the glucose sensor of the second earpiece;
   wherein the set of earpieces is configured to communicate the first glucose level and the second glucose level between the first earpiece and the second earpiece and compare the first glucose level from the glucose sensor of the first earpiece and the second glucose level from the glucose sensor of the second earpiece using at least one of the intelligent controls of the set of wireless earpieces to increase accuracy and detect error in the first glucose level and the second sensed glucose level; and
   wherein the set of wireless earpieces is configured to compare at least one of the first glucose level and the second glucose level to a threshold glucose level.

2. The set of earpieces of claim 1 further comprising a wireless transceiver disposed within the earpiece housing of each of the first earpiece and the second earpiece, the wireless transceiver operatively connected to the intelligent control; wherein the wireless transceiver disposed of within the earpiece housing of each of the first earpiece and the second earpiece is configured to communicate data between the set of earpieces.

3. The set of earpieces of claim 2 wherein the glucose sensor is a non-invasive glucose sensor.

4. The set of earpieces of claim 3 wherein the glucose sensor is a near infrared glucose sensor.

5. The set of earpieces of claim 1 wherein each of the first earpiece and the second earpiece further comprises:
   a speaker operably coupled to the intelligent control; and
   a microphone operably coupled to the intelligent control;
   wherein the intelligent control disposed within the earpiece housing is configured to play music and/or audio.

6. A method of glucose monitoring of an individual using a set of earpieces, the method comprising:
   providing the earpieces, each of the earpieces comprising an earpiece housing, an intelligent control disposed within the earpiece housing, a transceiver and a glucose sensor operatively connected to the intelligent control, the glucose sensor configured to be positioned against a wall of an external auditory canal of the individual;
   sensing a first glucose level of the individual by a first of the earpieces at a first external auditory canal of a first ear of the individual using the glucose sensor of the first of the earpieces and sensing a second glucose level of the individual by a second of the earpieces at a second external auditory canal of a second ear of the individual using the glucose sensor of the second of the earpieces;
   communicating the sensed first glucose level from the first of the earpieces within the set of earpieces to the second of the earpieces within the set of earpieces by the transceiver of the first of the earpiece operatively connected to the intelligent control; and
   comparing the sensed first glucose level from the first of the earpieces and the second glucose level of the second of the earpieces by the intelligent control of the second of the earpieces to determine differences in the first glucose level and the second glucose level to increase accuracy and/or detect error in the first glucose level and the second glucose level.

7. The method of claim 6 further comprising wirelessly communicating the at least one of the first glucose level and the second glucose level of the individual from the earpieces to a mobile device using the transceiver disposed within the earpiece housing of one of the each of the earpieces, the transceiver operatively connected to the intelligent control.

8. The method of claim 7, wherein the glucose sensor is non-invasive.

9. The method of claim 8, wherein the glucose sensor provides continuous measurement.

10. The method of claim 8, wherein the glucose sensor utilizes near infrared monitoring.

* * * * *